United States Patent
Soundararajan et al.

(10) Patent No.: US 9,308,346 B2
(45) Date of Patent: Apr. 12, 2016

(54) DEVICES AND METHODS FOR CRIMPING AND LOADING A COLLAPSIBLE DEVICE INTO A DELIVERY SYSTEM

(71) Applicant: Medtronic, Inc., Minneapolis, MN (US)

(72) Inventors: Gopikrishnan Soundararajan, Irvine, CA (US); Christopher Webster, Tustin, CA (US); Kenny Dang, Santa Ana, CA (US); Hussain Rangwala, Santa Ana, CA (US)

(73) Assignee: Medtronic, Inc., Minneapolis, MN (US)

( * ) Notice: Subject to any disclaimer, the term of this patent is extended or adjusted under 35 U.S.C. 154(b) by 343 days.

(21) Appl. No.: 13/757,359

(22) Filed: Feb. 1, 2013

(65) Prior Publication Data
US 2014/0215791 A1    Aug. 7, 2014

(51) Int. Cl.
*B25B 27/00* (2006.01)
*A61M 25/00* (2006.01)
*A61F 2/95* (2013.01)
*A61F 2/24* (2006.01)

(52) U.S. Cl.
CPC .............. *A61M 25/0009* (2013.01); *A61F 2/95* (2013.01); *A61F 2/24* (2013.01); *A61F 2002/9522* (2013.01); *Y10T 29/49826* (2015.01); *Y10T 29/53* (2015.01)

(58) Field of Classification Search
CPC .............. B66C 1/28; B66C 1/34; B66C 1/59; B66C 3/04; B66C 17/14
See application file for complete search history.

(56) References Cited

U.S. PATENT DOCUMENTS

| | | | | |
|---|---|---|---|---|
| 1,580,416 | A | * | 4/1926 | Cromwell et al. ............ 294/115 |
| 1,927,528 | A | * | 9/1933 | Nilsson ............................ 81/3.8 |
| 5,611,587 | A | * | 3/1997 | Brown ........................... 294/106 |
| 5,626,604 | A | | 5/1997 | Cottone, Jr. |
| 5,672,169 | A | | 9/1997 | Verbeek |
| 5,931,851 | A | | 8/1999 | Morales |
| 5,951,540 | A | | 9/1999 | Verbeek |
| 5,992,000 | A | | 11/1999 | Humphrey et al. |
| 6,009,614 | A | | 1/2000 | Morales |
| 6,018,857 | A | | 2/2000 | Duffy et al. |
| 6,024,737 | A | | 2/2000 | Morales |
| 6,051,002 | A | | 4/2000 | Morales |
| 6,063,092 | A | | 5/2000 | Shin |
| 6,063,102 | A | | 5/2000 | Morales |
| 6,360,577 | B2 | | 3/2002 | Austin |
| 6,609,283 | B1 | * | 8/2003 | Somerville ...................... 29/262 |
| 6,629,350 | B2 | | 10/2003 | Motsenbocker |

(Continued)

FOREIGN PATENT DOCUMENTS

WO    WO2010/130789    11/2010

OTHER PUBLICATIONS

PCT/US2014/014097, PCT Search Report and Written Opinion, mailed Apr. 29, 2014.

*Primary Examiner* — Lee D Wilson

(57) ABSTRACT

A device for crimping an collapsible device and loading the collapsible device into a delivery system, includes a crimping tool configured to radially crimp at least a portion of the collapsible device, a loading tool configured to load at least a portion of the collapsible device into a delivery system, and a housing that houses at least one of the crimping tool and loading tool, wherein the device is configured to crimp and load the collapsible device without requiring manual repositioning of the collapsible device. Methods of crimping an collapsible device and loading the collapsible device into a delivery system are also disclosed.

17 Claims, 13 Drawing Sheets

(56) References Cited

U.S. PATENT DOCUMENTS

| | | |
|---|---|---|
| 6,730,118 B2 | 5/2004 | Spenser et al. |
| 6,925,847 B2 | 8/2005 | Motsenbocker |
| 6,983,522 B2 * | 1/2006 | Weller et al. .................... 29/268 |
| 7,117,573 B1 * | 10/2006 | Hu ................................. 29/261 |
| 7,334,798 B2 * | 2/2008 | Halliburton .................. 273/447 |
| 7,530,253 B2 | 5/2009 | Spenser et al. |
| 8,978,221 B1 * | 3/2015 | Somerville et al. ............. 29/261 |
| 2002/0138966 A1 | 10/2002 | Motsenbocker |
| 2003/0070682 A1 | 4/2003 | Wilson et al. |
| 2003/0135970 A1 | 7/2003 | Thornton |
| 2003/0225445 A1 | 12/2003 | Derus et al. |
| 2004/0128818 A1 | 7/2004 | Motsenbocker |
| 2004/0148007 A1 | 7/2004 | Jackson et al. |
| 2006/0004469 A1 | 1/2006 | Sokel |
| 2007/0056346 A1 | 3/2007 | Spenser et al. |
| 2007/0239271 A1 | 10/2007 | Nguyen |
| 2008/0058916 A1 | 3/2008 | Huang et al. |
| 2008/0071362 A1 | 3/2008 | Tuval et al. |
| 2009/0018570 A1 | 1/2009 | Righini et al. |
| 2009/0093876 A1 | 4/2009 | Nitzan et al. |
| 2010/0036484 A1 | 2/2010 | Hariton et al. |
| 2010/0292779 A1 | 11/2010 | Straubinger et al. |
| 2012/0101569 A1 | 4/2012 | Mearns et al. |
| 2014/0215790 A1 | 8/2014 | Soundararajan et al. |
| 2015/0101635 A1 * | 4/2015 | Shnol ................................ 134/6 |

* cited by examiner

DEVICES AND METHODS FOR CRIMPING AND LOADING A COLLAPSIBLE DEVICE INTO A DELIVERY SYSTEM

BACKGROUND

1. Field

The present invention can relate to devices and methods for crimping and loading a collapsible device into a delivery system.

2. Background

Recently, minimally invasive approaches have been developed to facilitate surgical and catheter-based implantation of prostheses. For example, during transcatheter collapsible device implantations, a collapsible device is radially contracted onto a delivery catheter so that the collapsible device can be introduced into a body lumen, for example, into the femoral artery, the subclavian artery, or the aorta, or into a body cavity, for example, a chamber of the heart (e.g., the ventricle). Using the delivery catheter, the collapsible device can be guided to a desired implantation site through the body lumen or body cavity. Current methods for crimping and loading the collapsible device can be tedious and can potentially damage the collapsible device. Improved systems for crimping and loading a collapsible device for use in such delivery systems are desired.

BRIEF SUMMARY

In some embodiments, a device for crimping a collapsible device and loading the collapsible device into a delivery system can include a crimping tool configured to radially crimp at least a portion of the collapsible device, a loading tool that can be configured to load at least a portion of the collapsible device into a delivery system, and a housing that can house at least one of the crimping tool and loading tool. The device can be configured to crimp and load the collapsible device without requiring manual repositioning of the collapsible device.

In some embodiments, a method of crimping a collapsible device and loading the collapsible device into a delivery system can include obtaining a crimping and loading device including a crimping tool that can be configured to radially crimp at least a portion of the collapsible device, a loading tool that can be configured to load at least a portion of the collapsible device into a delivery system, and a housing that can house at least one of the crimping tool and loading tool. The device can be configured to crimp and load the collapsible device without requiring manual repositioning of the collapsible device. The crimping tool can include an actuator configured to actuate the crimping tool to radially crimp at least a portion of the collapsible device when the actuator is moved a predetermined amount relative to the housing. The crimping tool can include an actuator configured to actuate the loading tool to load at least a portion of the collapsible device into the delivery system when the actuator is moved a predetermined amount relative to the housing. The method can include moving the actuator a predetermined amount relative to the housing to crimp the collapsible device.

Some embodiments of the invention can result in more accurate deployment of the collapsible device during the delivery process. Some embodiments can minimize or prevent damage to the collapsible device, which can result in better performance and patient satisfaction. In some embodiments, a user can only to apply a force with their hands in a single direction to perform the complete crimping and loading operation.

BRIEF DESCRIPTION OF THE FIGURES

The accompanying figures, which are incorporated herein, form part of the specification and illustrate embodiments of the invention. Together with the description, the figures further serve to explain the principles of and to enable a person skilled in the relevant art(s) to make and use the devices and methods described herein.

DETAILED DESCRIPTION

The following detailed description of devices and methods for crimping and loading a collapsible device into a delivery system refers to the accompanying figures that illustrate certain embodiments. Other embodiments are possible. Modifications can be made to the embodiments described herein without departing from the spirit and scope of the present invention. Therefore, the following detailed description is not meant to be limiting. Further, it would be apparent to one of skill in the art that the devices and methods described below can be implemented in many different embodiments of hardware. Any actual hardware described is not meant to be limiting. The operation and behavior of the devices and methods presented are described with the understanding that modifications and variations of the embodiments are possible.

Figure 1:
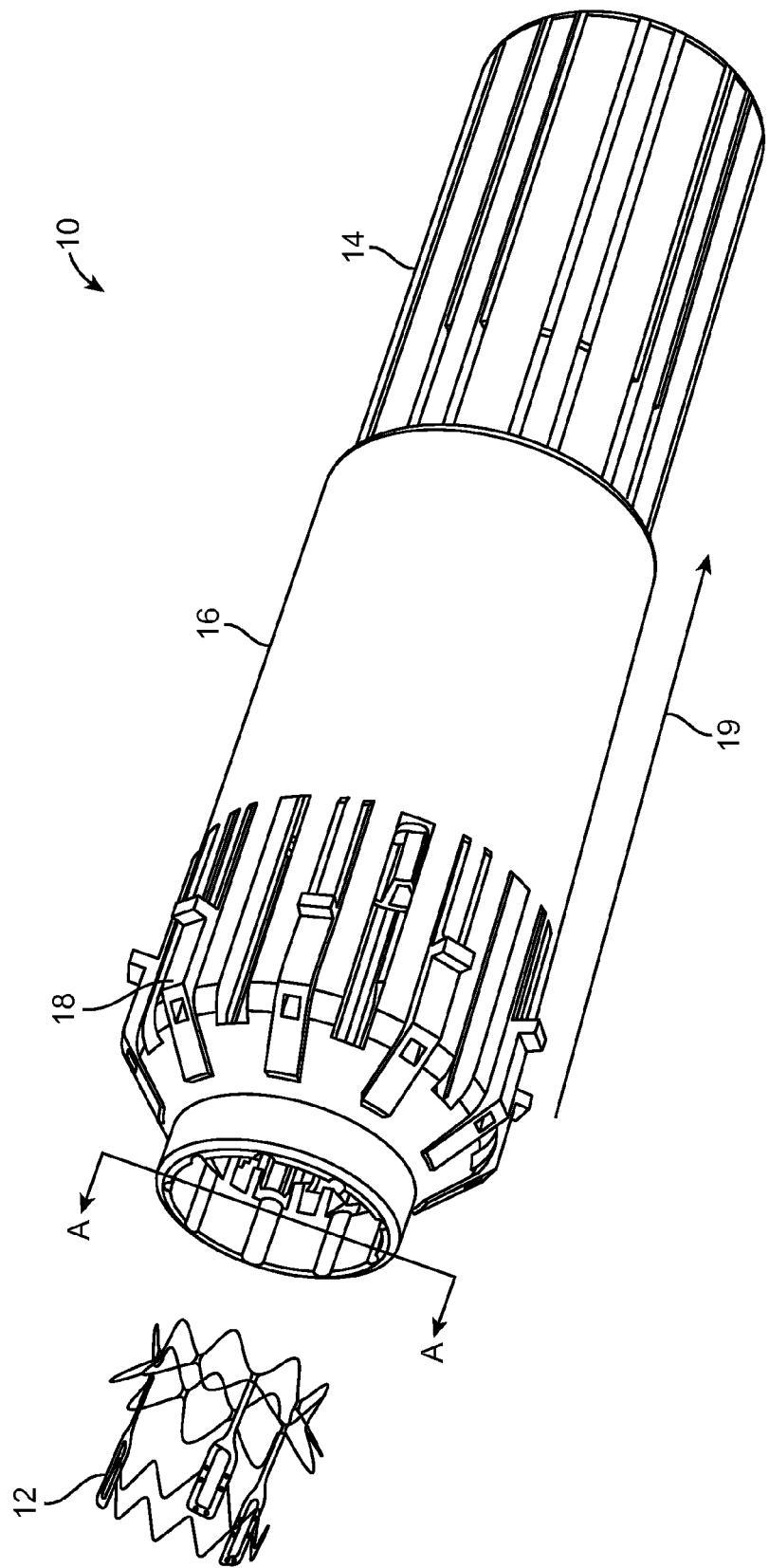
FIG. 1 illustrates a front perspective view of a crimping and loading device.

FIG. 1 illustrates a front perspective view of a crimping and loading device 10 along with a collapsible device 12. Collapsible device 12 can, for example, be a fully collapsible or partially collapsible device. In some embodiments, collapsible device 12 can be a medical device, such as one configured to be introduced into one or more body lumens or body cavities, such as for example a femoral artery, a subclavian artery, an aorta, a chamber of the heart, and/or a ventricle. In some embodiments, collapsible device 12 can be in the form of a compressible stent or frame for use in surgical, transcatheter, and/or trans-apical heart valve procedures. Collapsible device 12 can include, for example, a compressible prosthetic heart valve attached to a compressible frame. In some embodiments, collapsible device 12 can be a device for use in trans-catheter procedures, such as for example embolic filters or embolic filter retrievers. The collapsible device can also be a non-implantable device. For example, in some embodiments, the device can be an embolic filter that is not designed to be implanted within the patient's body. In some embodiments, the device can be a tool that can be used, for example, to retrieve an item from inside a patient. Collapsible devices are not limited to medical devices, and can broadly include any suitable devices desired to be crimped and loaded in a delivery system.

As will be described further herein, device 10 can include a base 14, an actuator 16, and compression elements 18 disposed within actuator 16. In operation, collapsible device 12 can be placed in a cavity formed between compression elements 18 within actuator 16. In some embodiments, before collapsible device 12 is placed within the cavity, it can be submerged in an ice and water bath and chilled for 30-60 seconds. Device 10 can be configured such that when actuator 16 is slid along base 14 in an axial direction 19, compression elements 18 are moved radially inward. Radially-inward-facing surfaces of compression elements 18 can be configured to gently and securely compress collapsible device 12 to a predetermined compressed state when compression elements 18 are moved radially inward.

In some embodiments, once collapsible device 12 is in a predetermined compressed state, device 10 can be configured such that certain relative movement between actuator 16 and base 14 will result in collapsible device 12 being moved in an axial direction opposite of axial direction 19 out from between compression elements 18. In some embodiments, collapsible device 12 can be moved out from between compression elements 18 and at least a portion of collapsible device 12 is loaded into a delivery system. Suitable delivery systems can include catheters for use in one or more transcatheter procedures, such as for example, angioplasty or transcatheter valve implantation.

Figure 2:
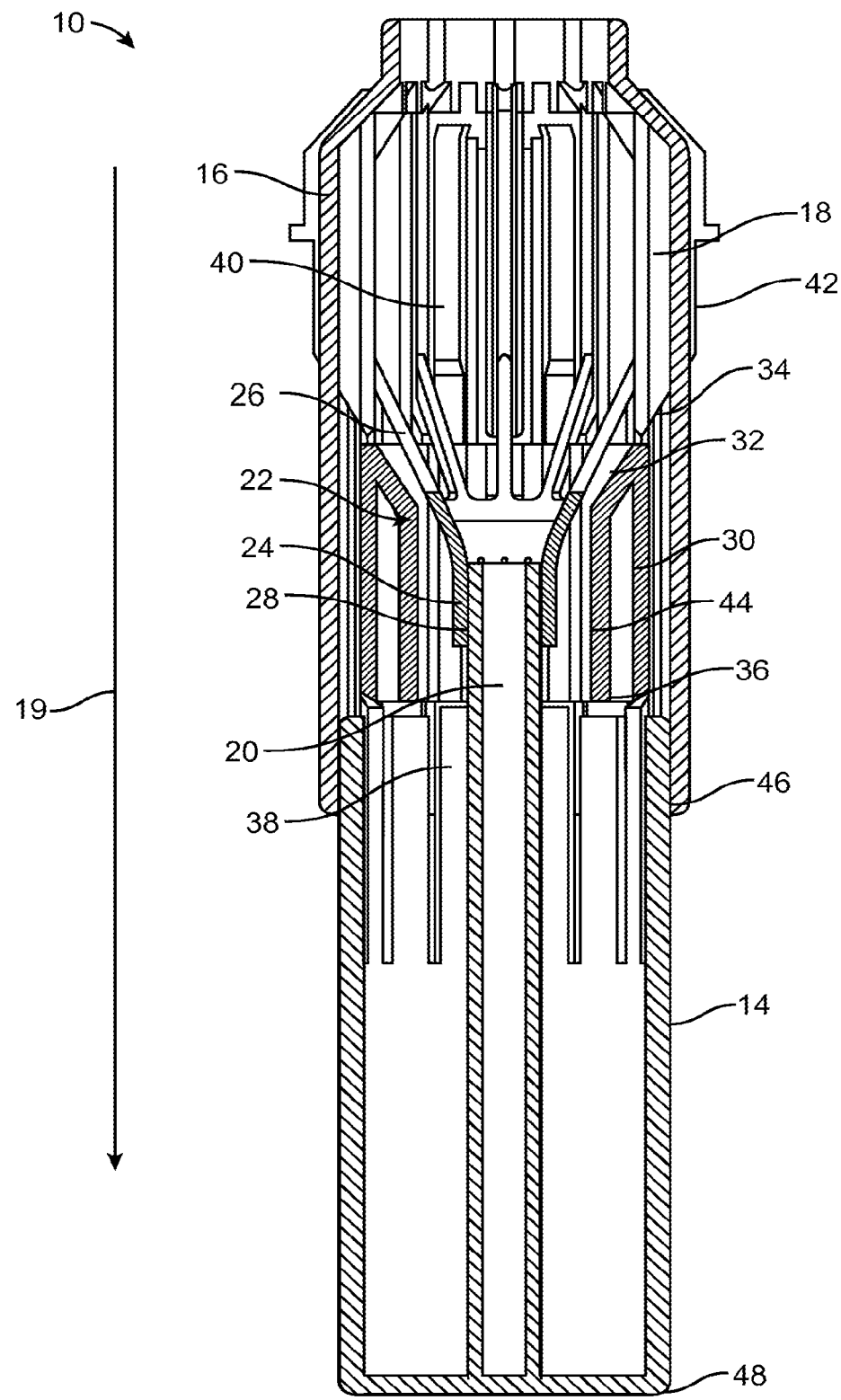
FIG. 2 illustrates a cross-sectional view of the device of FIG. 1 along line A-A.

FIG. 2 illustrates a cross-sectional view of device 10 along line A-A. As shown in this view, base 14 can include a post 20 that protrudes upward from a floor of base 14. Post 20 can be coupled with an expander 22 including an expander base 24 and a plurality of fingers 26 attached thereto. Expander 22 can be coupled to compression elements 18 and can be configured to radially bias compression elements 18 against actuator 16 via one or more of the plurality of fingers 26. Expander base 24 can be substantially cylindrical shaped and includes an opening 28 that is configured to permit post 20 to slide within and through expander 22. Although expander base 24 is substantially cylindrical in some embodiments, in other embodiments it can be square, pentagonal, heptagonal, octagonal, non-geometric, or the like. In some embodiments, the opening is circular. In some embodiments, it can be square, pentagonal, heptagonal, octagonal, non-geometric, or the like.

Device 10 can further include a sleeve 30. Sleeve 30 can be disposed within actuator 16 and can include a slanted surface 32 configured to engage with a corresponding slanted surface 34 of compression element 18 as well one or more of the plurality of fingers 26. Sleeve 30 can further include a bottom surface 36 configured to be selectively supported by arms 38 formed within base 14. Arms 38 can be outwardly biased but temporarily biased inwardly to fit within actuator 16 when device 10 is fully assembled. When arms 38 are biased inwardly to fit within actuator 16 in a fully assembled device 10, they can abut sleeve 30 and prevent movement of sleeve 30 in axial direction 19 relative to base 14. When actuator 16 is slid sufficiently down base 14, arms 38 can be allowed to radially expand through openings 40 formed within actuator 16. When arms 38 radially expand through openings 40, arms 38 can disengage from sleeve 30 and allow axial movement between sleeve 30 and base 14.

In an example crimping operation, actuator 16 can be moved in axial direction 19, which can force compression elements 18 to move along with actuator 16 in axial direction 19. When slanted surface 34 of compression element 18 reaches slanted surface 32 of sleeve 30, compression element 18 can be moved radially inwardly against a resistive force from the plurality of fingers 26 of expander 22. The lengths of slanted surface 32 and slanted surface 34 can be configured to permit compression of collapsible device 12 to a desired compressed state (e.g., a desired compressed diameter). In this embodiment, once the desired compressed state is reached, additional axial movement of actuator 16 will not result in additional radial movement of compression element 18 and therefore will not result in additional compression of collapsible device 12. For example, vertical surface 42 of compression element 18 can be configured to slide along a corresponding vertical surface 44 of sleeve 30 once compression element 18 moves a predetermined radial and axial distance along slanted surface 32 of sleeve 30.

In an example loading operation, actuator 16 can be slid down base 14 until arms 38 reach openings 40 of actuator 16. Once this occurs, arms 38 can radially expand through openings 40, which can allow for arms 38 to disengage from sleeve 30. This disengagement can allow post 20 to slide through both sleeve 30 and expander 22 and push collapsible device 12 out from between compression elements 18.

Device 10 can be configured such that the above crimping and loading process can be complete when a bottom end 46 of actuator 16 is flush with a bottom end 48 of base 14. In some embodiments, such a configuration can assist a user in determining when the crimping and loading process is complete. In some embodiments, the crimping and loading process can be complete before or after bottom end 46 is flush with bottom end 48.

As described above for example, actuator 16 can be configured to actuate compression elements 18 to radially crimp at least a portion of collapsible device 12 when actuator 16 is moved from a first predetermined position relative to base 14 to a second predetermined position relative to base 14. Actuator 16 can further be configured to actuate base 14 to load at least a portion of collapsible device 12 into a delivery system when actuator 16 is moved from the second predetermined position relative to base 14 to a third predetermined position relative to base 14. In some embodiments, actuator 16 can be configured to actuate base 14 to load at least a portion of collapsible device 12 into a delivery system when actuator 16 is moved in a second and opposite axial direction from a third predetermined position relative to base 14 to a fourth predetermined position relative to base 14. In some embodiments, the second predetermined position can be the same as the third predetermined position. In some embodiments, the first predetermined position can be the same as the fourth predetermined position.

Figure 3:
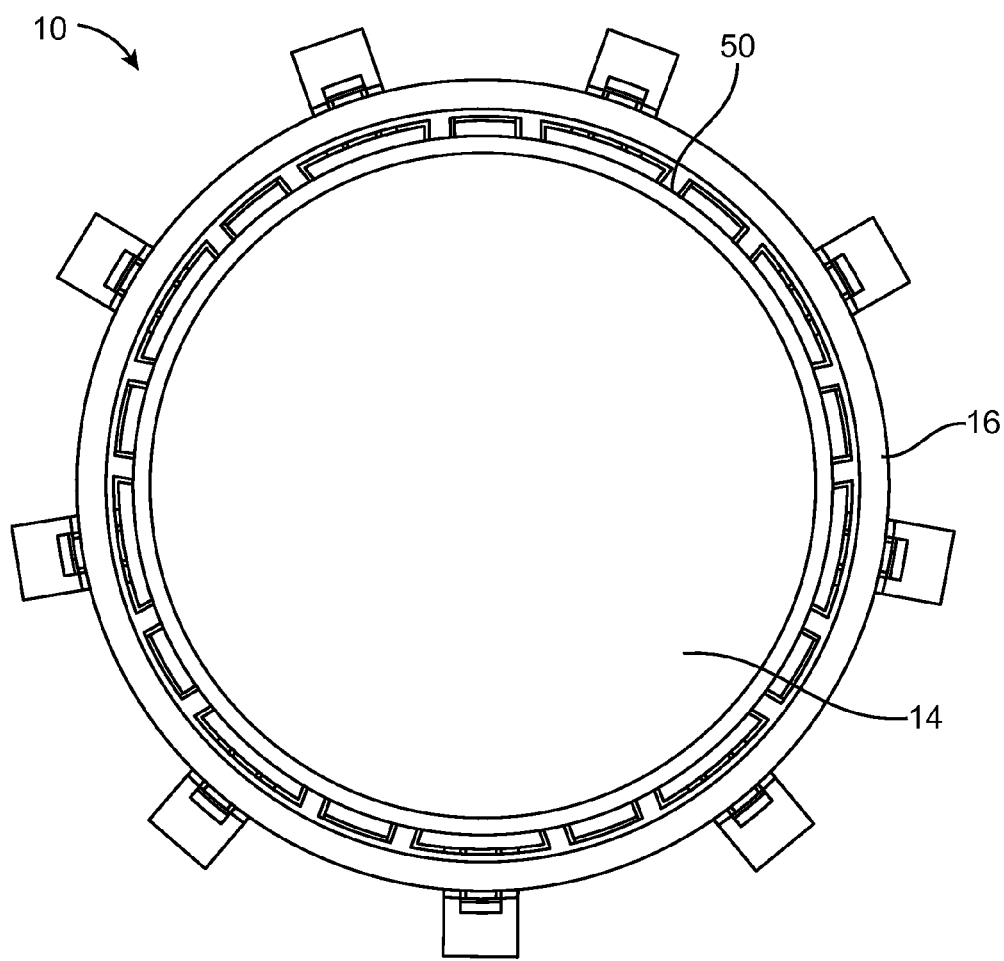
FIG. 3 illustrates a bottom view of the device of FIG. 1.

FIG. 3 illustrates a bottom view of device 10. Actuator 16 and base 14 can form a tongue-and-groove joint 50 to allow relative axial movement between actuator 16 and base 14 while preventing relative rotational movement therebetween. Device 10 can include a plurality of tongue-and-groove joints 50 spread substantially uniformly around base 14. In some embodiments, a single tongue-and-groove joint 50 can be used. Other suitable configurations can be used to restrict or prevent relative movement between actuator 16 and base 14. For example, in some embodiments, tongue-and-groove joint 50 can be configured to allow for rotational movement in a first rotational direction while preventing rotational movement in an opposite direction. In some embodiments, actuator 16 and base 14 do not include a tongue-and-groove arrangement. In some embodiments, actuator 16 can be rotated relative to base 14.

Figure 4:
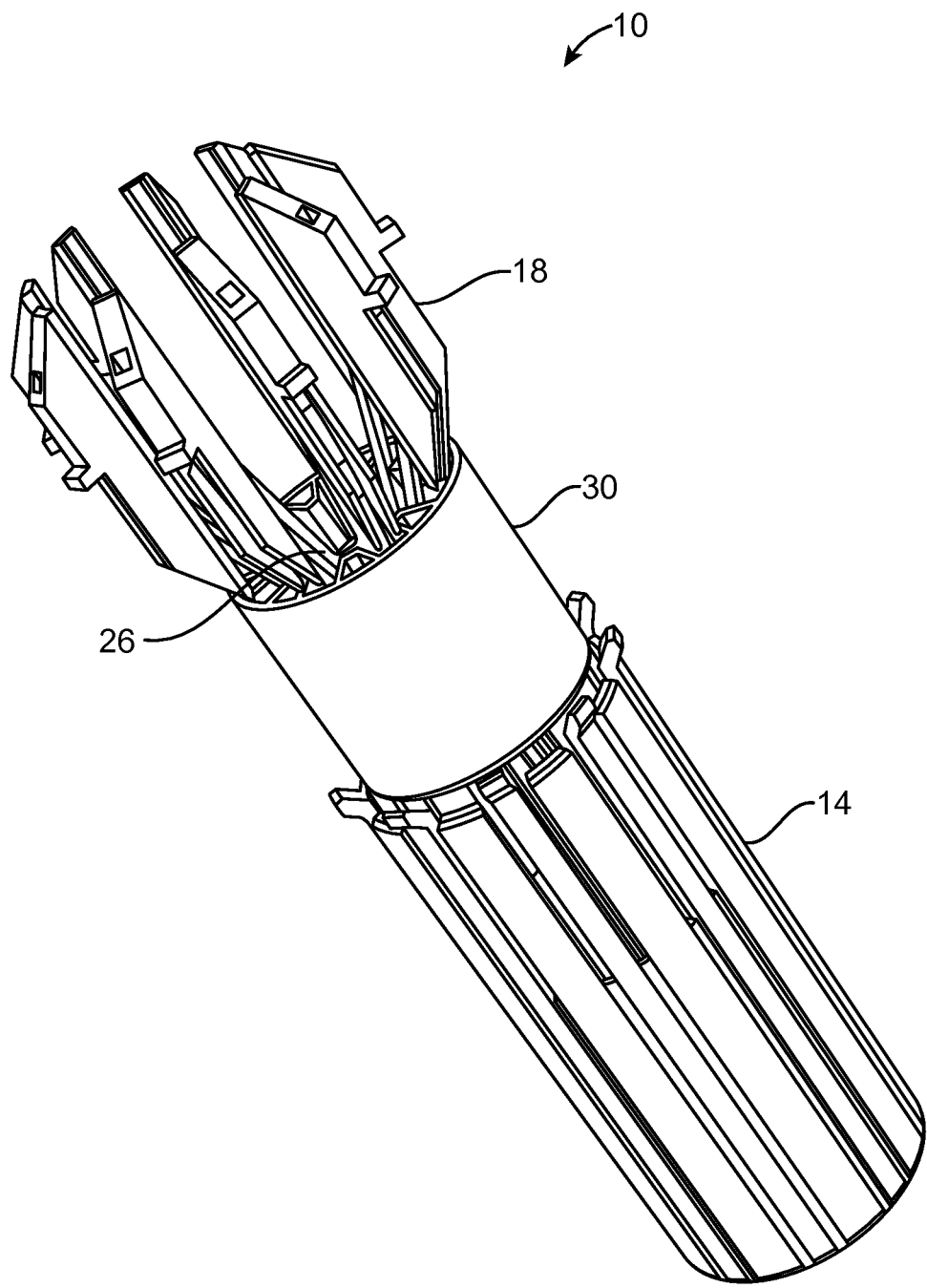
FIG. 4 illustrates a front perspective view of the device of FIG. 1 with its actuator removed for clarity.
Figure 5:
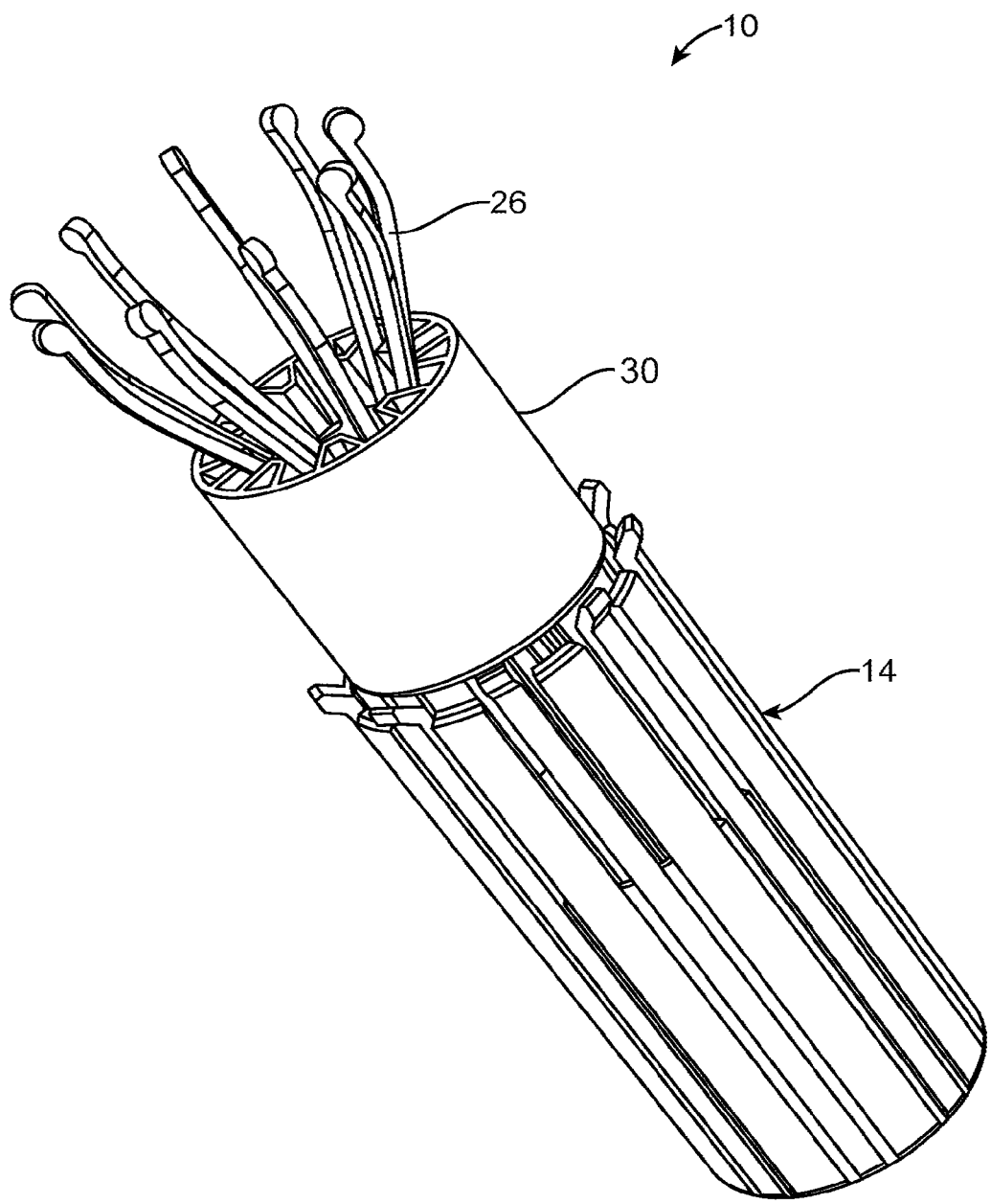
FIG. 5 illustrates a front perspective view of the device of FIG. 1, with its actuator and compression elements removed for clarity.

FIG. 4 illustrates a front perspective view of device 10 with actuator 16 removed for clarity. FIG. 5 illustrates a front perspective view of device 10 with actuator 16 and compression elements 18 removed for clarity.

In the embodiments described above, compression elements 18 and actuator 16 can together serve as a crimping tool for radially crimping at least a portion of collapsible device 12. Post 20 can serve as a loading tool for loading at least a portion of collapsible device 12 into a delivery system. Base 14 can serve as a housing that houses at least one of compression elements 18, actuator 16, and post 20.

One or more of the crimping and loading tool can be configured to provide a mechanical advantage, such as greater leverage, compared to manual crimping or loading techniques. This can be especially useful for example when large crimping forces are desired, such as when crimping a device for use in certain small-diameter catheters. In some embodiments, the crimping tool can include a lever arm or attachment to provide one or more additional mechanical advantages. In some embodiments, one or more of the parts within the crimping or loading tool can be actuated (completely or partially) using hydraulic power, pneumatic power, or any suitable device capable of converting energy into mechanical motion. As an example, in some embodiments, the force exerted by the user during the crimping step is amplified by an electric motor housed within the device.

One or more of the devices described herein can be configured to crimp and load a collapsible device without requiring manual repositioning of the collapsible device following the crimping operation. For example, in some embodiments, the collapsible device can first be radially crimped via movement of an actuator in an axial or rotational direction relative to the base. Thereafter, in some embodiments, a user need only move the actuator in the same or opposite axial direction relative to the base or rotate the actuator relative to the base to perform the loading operation. In some embodiments, such a configuration can allow the user to use a single device to crimp and load the collapsible device. In some embodiments, such a configuration will not require that the user reposition the collapsible device within the device or move the collapsible device from one device to another subsequent to the crimping operation in order to perform the loading operation. In some embodiments, this can reduce the number of process steps required to crimp and load the collapsible device. Such a reduction in process steps can result in a reduction of time required to complete the crimping and loading operation and can reduce the possibility of damaging the collapsible device during the operation. In some embodiments, the crimping and loading steps can occur simultaneously.

Figure 6:
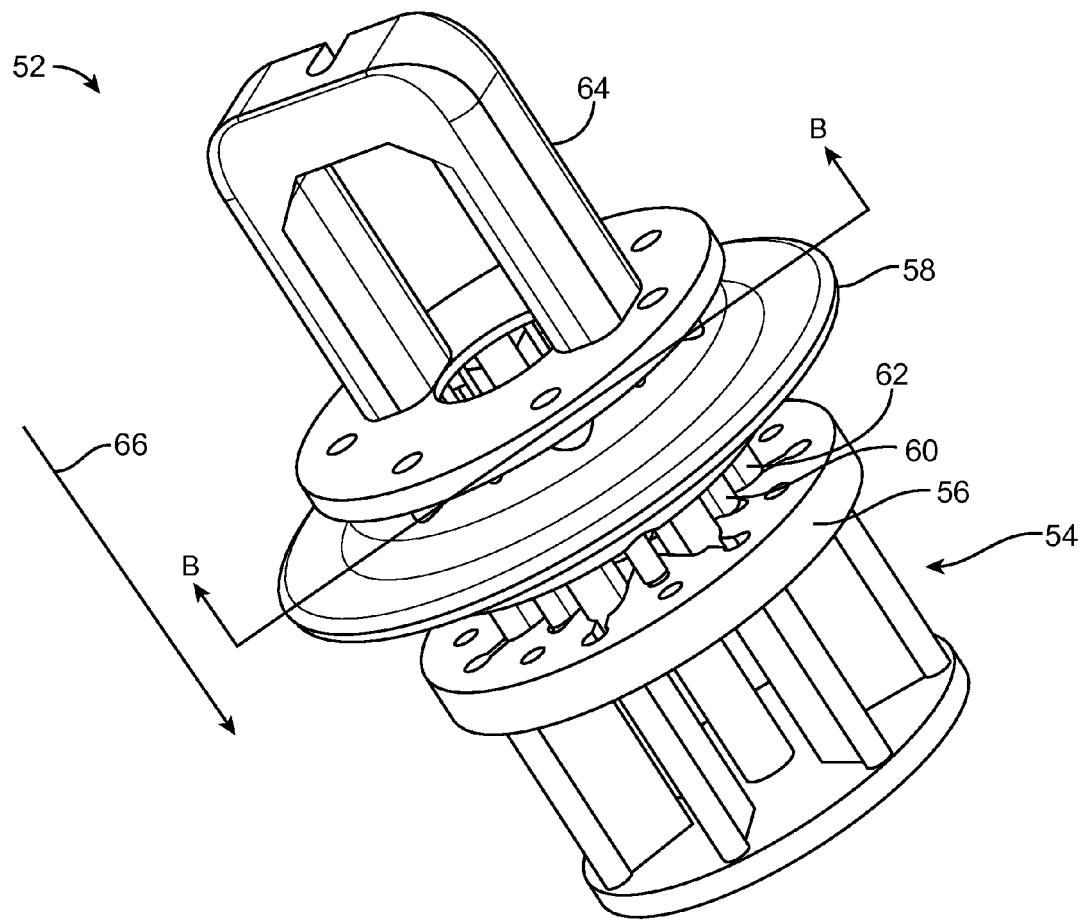
FIG. 6 illustrates a front perspective view of another crimping and loading device.

FIG. 6 illustrates a front perspective view of another embodiment of a crimping and loading device 52. Like device 10 described above with respect to FIGS. 1-5, device 52 can be configured to crimp and load a suitable collapsible device (such as, for example, collapsible device 12 described with respect to FIG. 1). As will be described further herein, device 52 can include a base 54, plate 56, actuator 58, compression elements (also referred to as "track cylinders 60" and "crimp cylinders 62"), and a top 64. In an example crimping operation, a collapsible device can be placed within a central cavity formed between track cylinders 60 and crimp cylinders 62. Actuator 58 can be configured to slide towards base 54 in axial direction 66. Device 52 can be configured such that when actuator 58 is slid towards base 54 in axial direction 66, crimp cylinders 62 and track cylinders 60 are pushed radially inward to compress the collapsible device to a predetermined compressed state. In some embodiments, a slanted surface can be formed on actuator 58 and can be configured to correspond to a slanted surface of crimp cylinder 62 and track cylinders 60 in order to provide radially inward movement of crimp cylinders 62 and track cylinders 60 when actuator is moved in axial direction 66 against actuator 58. In some embodiments, slanted surfaces of actuator 58, crimp cylinder 62, and track cylinder 60 can be in the form of tapered notches that push the crimp cylinders 62 and track cylinders 60 to a smaller diameter through abutment with actuator 58.

In some embodiments, top 64 can include a fixture that attaches to the delivery system. In some embodiments, top 64 can include holes that serve to facilitate radial movement of crimp cylinders 62 and track cylinders 60 and constrain movement in other directions.

In some embodiments, once the collapsible device is in the predetermined compressed state, device 52 is configured to allow base 54 to load the collapsible device directly into a catheter for use in a transcatheter procedure, such as for example, angioplasty or transcatheter valve implantation. In an example loading operation, actuator 58 can be slid to a predetermined position with respect to base 54. Device 52 can be configured such that when actuator 58 is slid to a predetermined position with respect to base 54, base 54 pushes the collapsible device out from between track cylinders 60 and crimp cylinders 62 to be loaded into a catheter or other desired location.

Figure 7:
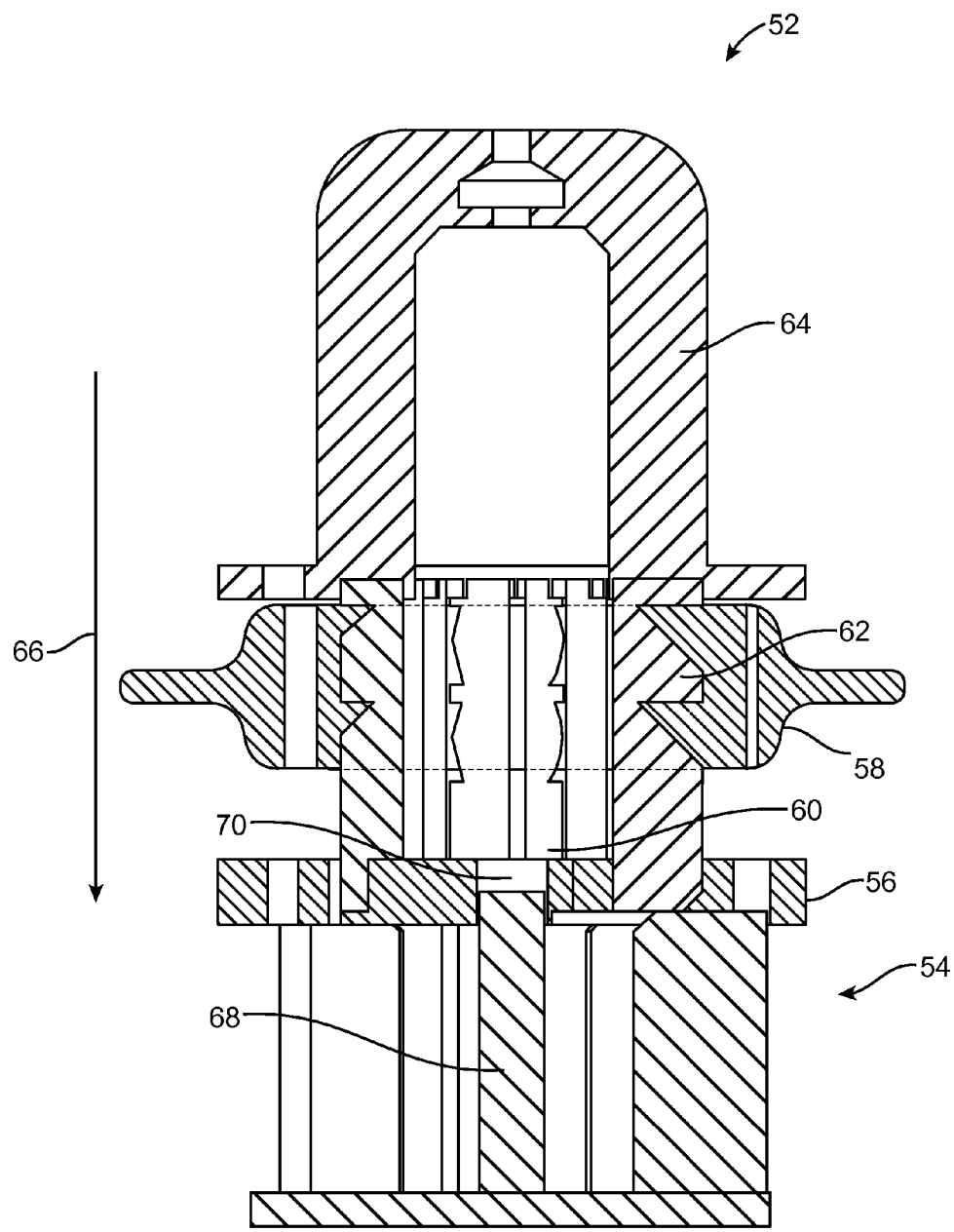
FIG. 7 illustrates a cross-sectional view of the device of FIG. 6 along line B-B.

FIG. 7 illustrates a cross-sectional view of device 52 along line B-B. As shown in this view, base 54 can include post 68, which can be coupled with plate 56. Plate 56 can include a central hole 70 formed therein that can be configured to permit post 68 to slide within and through plate 56. In certain embodiments, hole 70 can be circular. In other embodiments, hole 70 can be square, pentagonal, heptagonal, octagonal, non-geometric, or the like.

Figure 8:
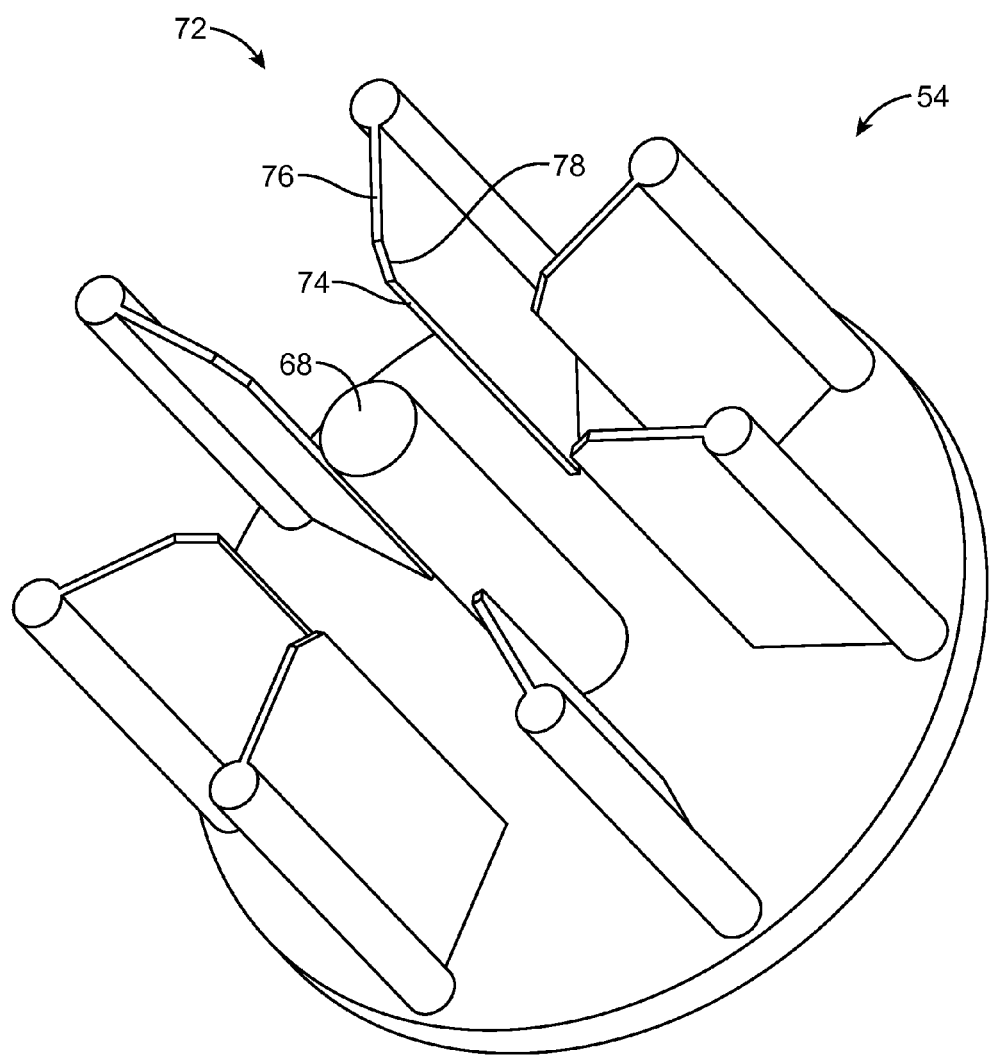
FIG. 8 illustrates a front perspective view of a base of the device of FIG. 6.

FIG. 8 illustrates a front perspective view of base 54. Base 54 can include a plurality of fins 72 disposed radially outward from post 68. Each fin 72 can include a vertical surface 74, horizontal surface 76, and slanted surface 78 configured to engage with corresponding surfaces of track cylinders 60 and crimp cylinders 62.

Figure 9:
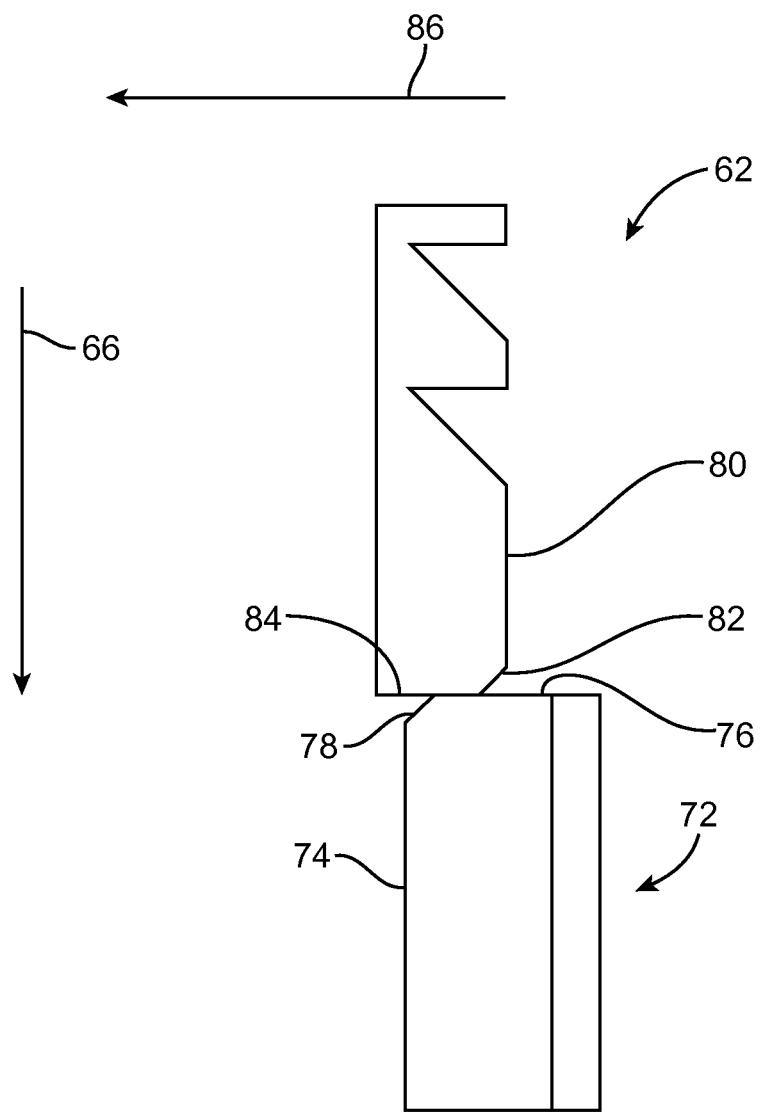
FIG. 9 illustrates a fin and crimp cylinder of the device of FIG. 6.

FIG. 9 illustrates an example of the coupling relationship between fin 72 and crimp cylinder 62 of device 52. As shown in FIG. 9, crimp cylinder 62 can include a vertical surface 80, slanted surface 82, and horizontal surface 84, which can be respectively configured to engage with corresponding vertical surface 74, slanted surface 78, and horizontal surface 76 of fin 72. In this embodiment, before crimp cylinder 62 is moved radially inward, horizontal surface 84 of crimp cylinder 62 abuts against with horizontal surface 76 of fin 72 to prevent movement in axial direction 66 relative to fin 72. As crimp cylinder 62 is moved in a radially inward direction 86, horizontal surfaces 84 and 76 continue to prevent movement in axial direction 66 until slanted surface 82 of crimp cylinder 62 reaches slanted surface 78 of fin 72. Once slanted surface 82 reaches slanted surface 78, crimp cylinder 62 can be permitted to also move in axial direction 66. As crimp cylinder 62 is moved in radially inward direction 86 and in axial direction 66, vertical surface 80 of crimp cylinder 62 can engage with vertical surface 74 of fin 72. This engagement can allow for axial movement between crimp cylinder 62 and fin 72 while preventing radially outward movement of crimp cylinder 62. In some embodiments, crimp cylinder 62 can be biased in a radially outward direction via a spring or other suitable mechanism.

Figure 10:
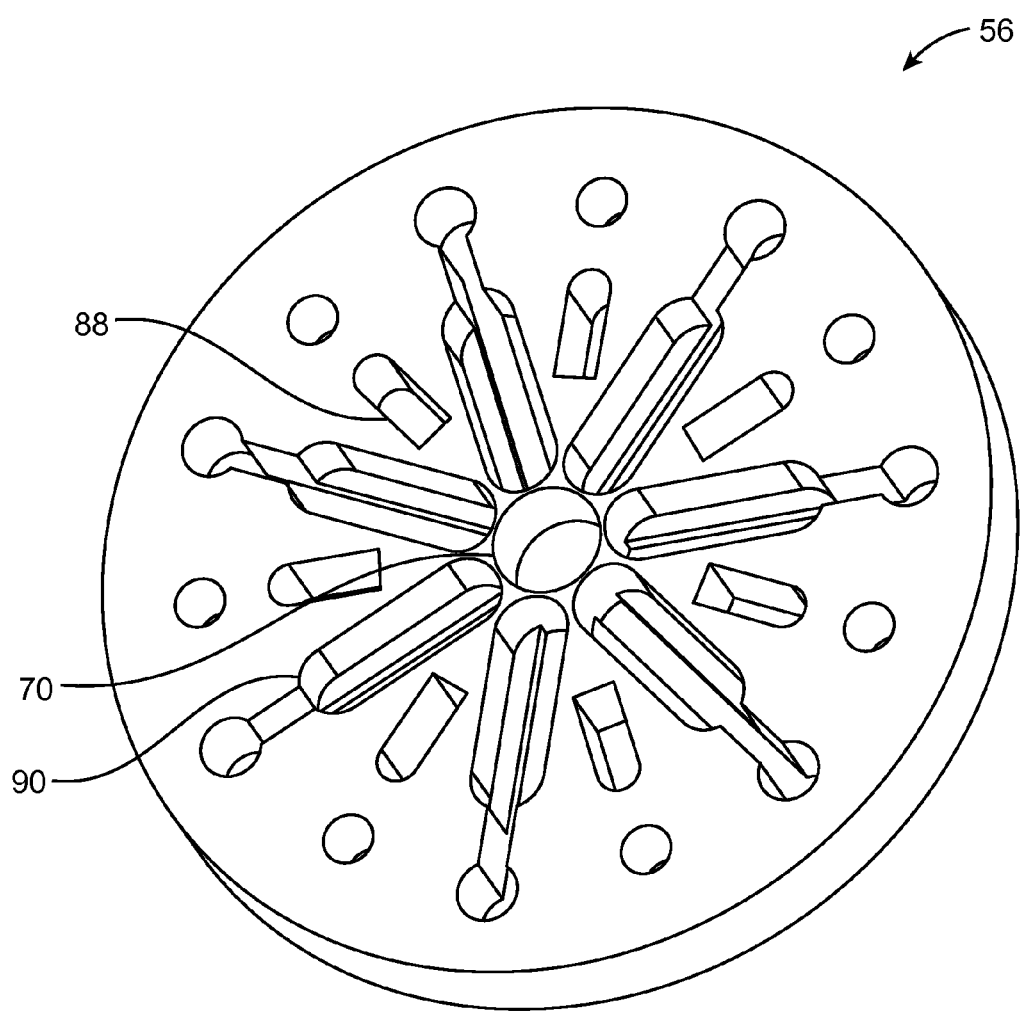
FIG. 10 illustrates a front perspective view of a plate of the device of FIG. 6.

FIG. 10 illustrates a perspective view of plate 56. Plate 56 can include a plurality of elongate holes 88 and 90, which can be configured to allow for respective radial movement of track cylinders 60 and crimp cylinders 62 relative to plate 56.

In an example loading operation, when track cylinders 60 and/or crimp cylinders 62 are allowed to move in axial direction 66 relative to fin 72, further movement of actuator 58 in axial direction 66 can allow post 68 to slide through hole 70 of plate 56 and push the collapsible device out from between track cylinders 60 and crimp cylinders 62. In some embodiments, the collapsible device can be pushed out from between track cylinders 60 and crimp cylinder 62 to load at least a portion of the collapsible device into a delivery system.

As described above, actuator 58 can be configured to actuate compression elements 60, 62 to radially crimp at least a portion of the collapsible device when actuator 58 is moved in an axial direction from a first predetermined position relative to base 54 to a second predetermined position relative to base 54. Actuator 58 can further be configured to actuate base 54 to load at least a portion of the collapsible device into a delivery system when actuator 58 is moved from the second predetermined position relative to base 54 to a third predetermined position relative to base 54. In some embodiments, actuator 58 can be configured to actuate base 54 to load at least a portion of the collapsible device into a delivery system when actuator 58 is moved in a second and opposite axial direction from a third predetermined position relative to base 54 to a fourth predetermined position relative to base 54. In some embodiments, the second predetermined position can be the same as the third predetermined position. In some embodiments, the first predetermined position can be the same as the fourth predetermined position.

In some embodiments, track cylinders 60 can be configured to move radially inward only half as much as crimp cylinders 62. In some embodiments, this can provide for improved centering of the collapsible device. In some embodiments, this can provide for improved contact of the collapsible device during the compression operation. In some embodiments, this can provide for a reduced possibility of circumferential buckling the collapsible device during the compression operation. In some embodiments, track cylinders 60 can be configured only to compress the collapsible device in a radially inward direction, but not move in an axial direction relative to plate 56.

In the embodiments described above, compression elements 60, 62 and actuator 58 can together serve as a crimping tool for radially crimping at least a portion of the collapsible device. Post 68 can serve as a loading tool for loading at least a portion of the collapsible device into a delivery system. Base 54 can serve as a housing that houses at least one of compression elements 60, 62, actuators 58, and post 68. Device 52 can be configured to crimp and load the collapsible device without requiring manual repositioning of the collapsible device following the crimping operation.

Figure 11:
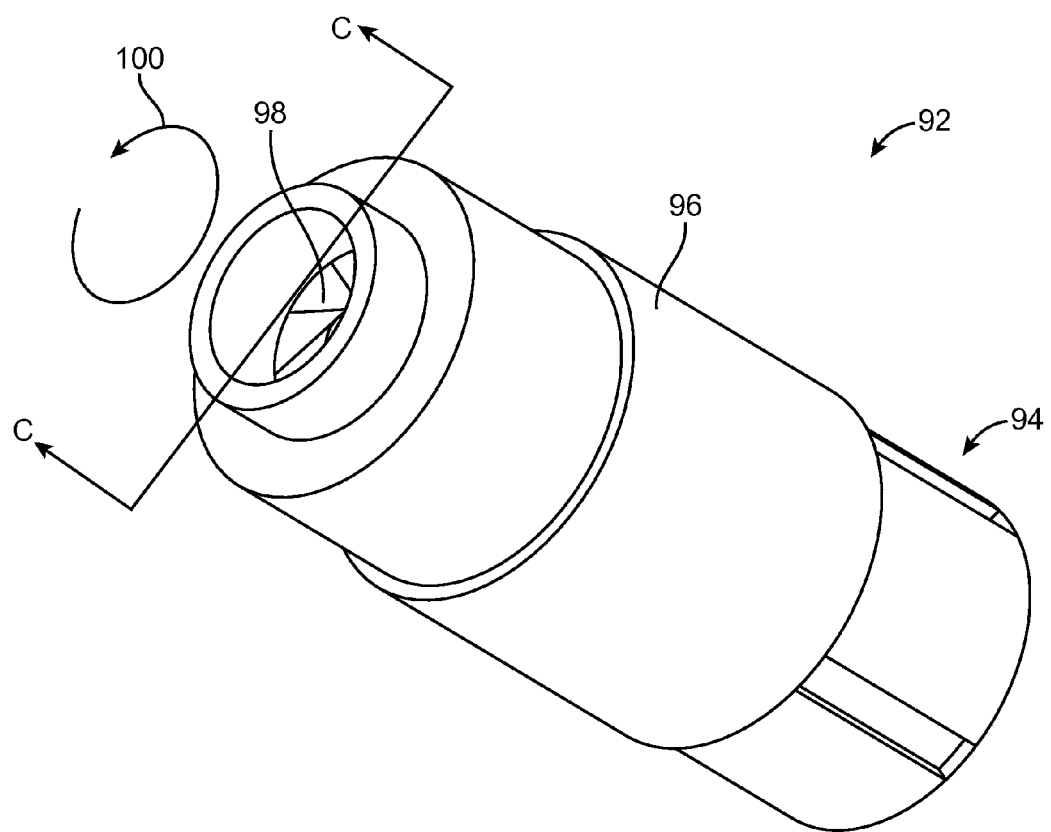
FIG. 11 illustrates a front perspective view of another crimping and loading device.

FIG. 11 illustrates a front perspective view of another embodiment of a crimping and loading device 92. Like device 10 and device 52 described above with respect to FIG. 1 and FIG. 6, device 92 can be configured to crimp and load a suitable collapsible device (such as, for example, collapsible device 12 described with respect to FIG. 1). As will be described further herein, device 92 can include a base 94, actuator 96, and compression elements 98. In an example crimping operation, a collapsible device can be placed within a central cavity formed between compression elements 98. Actuator 96 can then rotated relative to base 94 in rotation direction 100. Device 92 can be configured such that when actuator 96 is rotated relative to base 94 in rotation direction 100, compression elements 98 are moved radially inward to compress the collapsible device to a predetermined compressed state.

Figure 12:
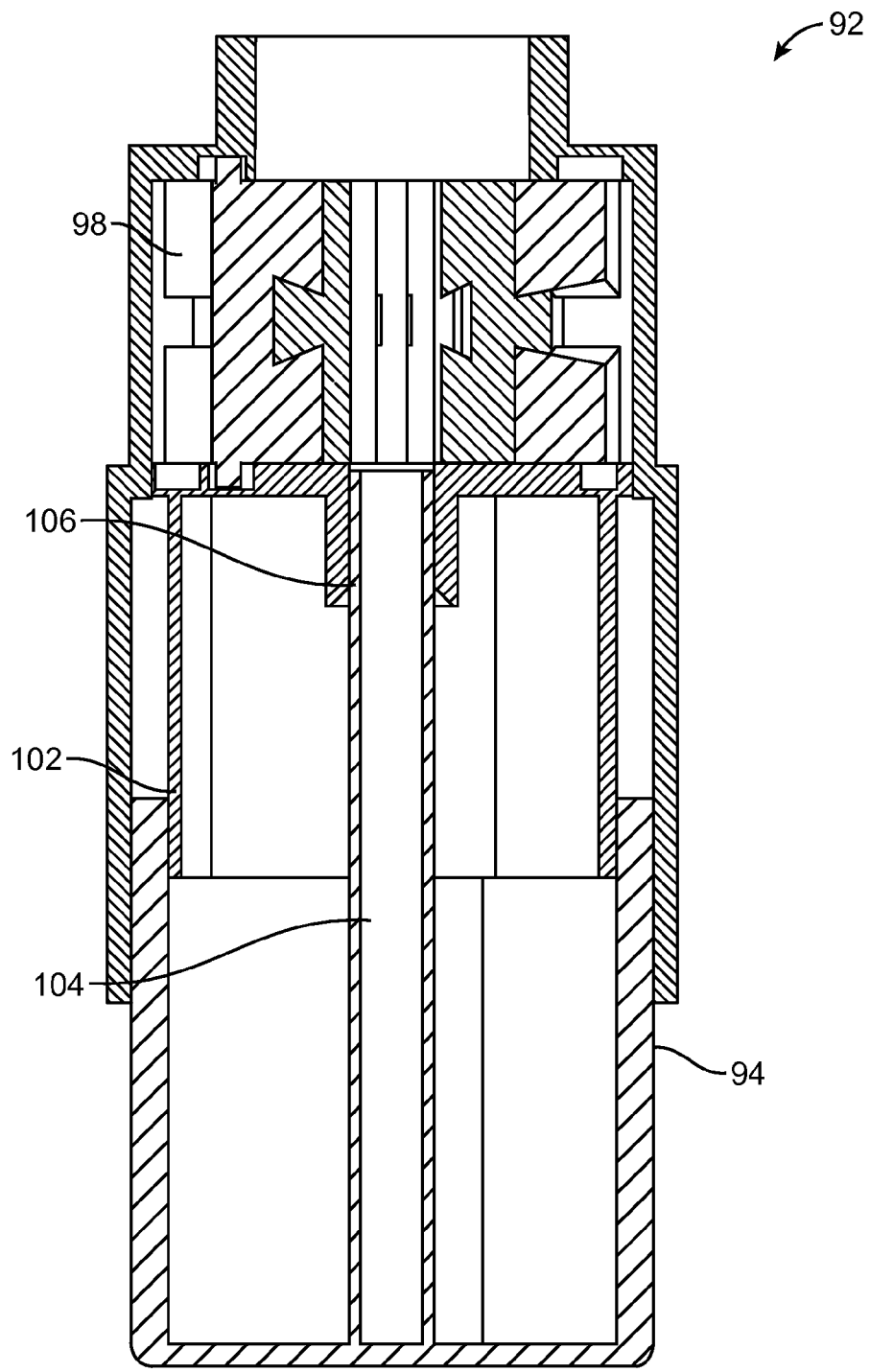
FIG. 12 illustrates a cross-sectional view of the device of FIG. 11 along line C-C.

FIG. 12 illustrates a cross-sectional view of device 92 along line C-C. As shown in this view, device 92 can include a sleeve 102 disposed between base 94 and compression elements 98. Base 94 can include a post 104 formed therein that is configured to couple with a circular hole 106 formed within sleeve 102 to permit post 104 to slide within and through sleeve 102.

Figure 13:
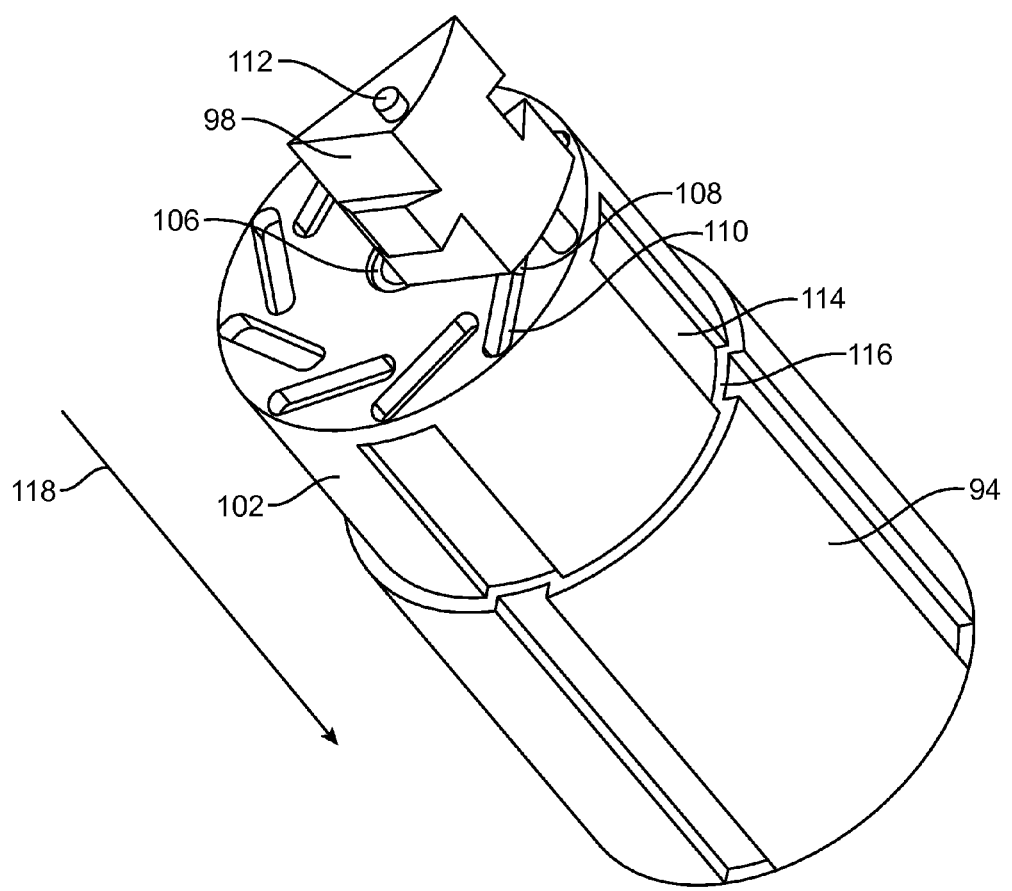
FIG. 13 illustrates a front perspective view of the device of FIG. 11, with its actuator and all but one of its compression elements removed for clarity.

FIG. 13 illustrates a front perspective view of device 92 with actuator 96 and all but one of compression elements 98 removed. Compression element 98 can include a first protrusion 108 that can be configured to be slidably disposed within a corresponding pill-shaped recess 110 in sleeve 102. Compression element 98 can include a second protrusion 112 that can be configured to be slidably disposed within a corresponding recess within an inner surface of actuator 96 (not shown). Actuator 96 can be coupled to compression element 98 such that rotation of actuator 96 relative to base 94 forces protrusions 108 and 112 of compression element 98 to travel along recess 110 and the recess within actuator 96, respectively. As compression element 98 travels along recess 110, compression element 98 is moved radially inward to crimp the collapsible device disposed between compression elements 98. When protrusion 108 of compression element 98 reaches an edge of recess 110, further rotation of actuator 96 relative to base 94 serves to rotate sleeve 102 relative to base 94. Sleeve 102 includes a groove 114 configured to mate with a corresponding tongue 116 of base 94 to form a tongue-and-groove relationship that permits axial movement between sleeve 102 and base 94 when tongue 116 is aligned with groove 114.

In an example loading operation, when sleeve 102 is allowed to move in axial direction 118 relative to base 94, movement of actuator 96 in axial direction 118 can allow post 104 to slide through hole 106 of sleeve 102 and push the collapsible device out from between compression elements 98. Actuator 96 can be configured to actuate compression elements 98 to radially crimp at least a portion of the collapsible device when actuator 96 is rotated a predetermined amount from a first predetermined position relative to base 94 to a second predetermined position relative to base 94. Actuator 96 can be further configured to actuate base 94 to load at least a portion of the collapsible device into a delivery system when actuator 96 is moved from the second predetermined position relative to base 94 to a third predetermined position relative to base 94. In some embodiments, actuator 96 can be configured to actuate base 94 to load at least a portion of the collapsible device into a delivery system when actuator 96 is moved in a second and opposite axial direction from a third predetermined position relative to base 94 to a fourth predetermined position relative to base 94. In some embodiments, the second predetermined position can be the same as the third predetermined position. In some embodiments, the first predetermined position can be the same as the fourth predetermined position.

In the embodiments described above, compression elements 98 and actuator 96 can together serve as a crimping tool for radially crimping at least a portion of the collapsible device. Post 104 can serve as a loading tool for loading at least a portion of the collapsible device into a delivery system. Base 94 can serve as a housing that houses at least one of compression elements 98, actuators 96, and post 104. Device 92 can be configured to crimp and load the collapsible device without requiring manual repositioning of the collapsible device following the crimping operation.

The choice of materials for the parts within devices 10, 52, and 92 can be informed by the requirements of mechanical properties, temperature sensitivity, biocompatibility, moldability properties, or any other factor apparent to a person having ordinary skill in the art. For example, one more of the parts (or a portion of one of the parts) can be made from suitable plastics, such as a suitable thermoplastic, suitable metals, and/or other suitable materials.

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments with modifications as are suited to the particular use contemplated. It is intended that the appended claims be construed to include other alternative embodiments of the invention.

We claim:

1. A device for crimping and loading a collapsible device into a delivery system, the device comprising:
   a crimping tool configured to radially crimp at least a portion of the collapsible device, the crimping tool including an actuator, a plurality of compression elements, and a central cavity formed by the compression elements, wherein the plurality of compression elements are configured such that axial movement of the actuator causes the compression elements to radially compress such that the central cavity radially compresses from an expanded configuration to a compressed configuration; and
   a loading tool configured to load at least a portion of the collapsible device into a delivery system, the loading tool including a rod, wherein the loading tool is configured for axial movement relative to the actuator such that the rod may enter the central cavity with the central cavity in the compressed configuration to push the collapsible device out of the central cavity and into the delivery system;
   wherein the device is configured to crimp and load the collapsible device without requiring manual repositioning of the collapsible device.

2. The device of claim 1,
   wherein the actuator is configured to actuate the crimping tool to radially crimp at least a portion of the collapsible device when the actuator is moved axially a predetermined amount relative to the loading tool.

3. The device of claim 1,
   wherein the actuator is configured to actuate the loading tool to load at least a portion of the collapsible device into the delivery system when the actuator is moved a predetermined amount relative to the loading tool.

4. The device of claim 3, wherein the actuator is configured to actuate the loading tool to load at least a portion of the collapsible device into the delivery system when the actuator is moved a predetermined amount in an axial direction relative to the loading tool.

5. The device of claim 1,
   wherein the actuator is configured to actuate the crimping tool to radially crimp at least a portion of the collapsible device when the actuator is moved from a first predetermined position relative to the loading tool to a second predetermined position relative to the loading tool,
   wherein the actuator is configured to actuate the loading tool to load at least a portion of the collapsible device into the delivery system when the actuator is moved from the second predetermined position relative to the loading tool to a third predetermined position relative to the loading tool.

6. The device of claim 1,
   wherein the actuator is configured to actuate the crimping tool to radially crimp at least a portion of the collapsible device when the actuator is moved from a first predetermined position relative to the loading tool to a second predetermined position relative to the loading tool,
   wherein the actuator is configured to actuate the loading tool to load at least a portion of the collapsible device into the delivery system when the actuator is moved from a third predetermined position relative to the loading tool to a fourth predetermined position relative to the loading tool.

7. The device of claim 1,
   wherein the actuator is configured to actuate the crimping tool to radially crimp at least a portion of the collapsible device when the actuator is moved in a first axial direction from a first predetermined position relative to the loading tool to a second predetermined position relative to the loading tool,
   wherein the actuator is configured to actuate the loading tool to load at least a portion of the collapsible device into the delivery system when the actuator is moved in a second and opposite axial direction from a third predetermined position relative to the loading tool to a fourth predetermined position relative to the loading tool.

8. The device of claim 7, wherein the second predetermined position is the same as the third predetermined position.

9. The device of claim 1, further comprising an expander, wherein the compression elements are coupled to the expander which biases the compression elements radially outwardly, wherein axial movement of the actuator overcomes the bias of the expanded to radially compress the compression elements.

10. The device of claim 9, wherein the expander includes a base configured to receive the post therethrough and plurality of fingers coupled to the compression elements.

11. The device of claim 10, further comprising a sleeve disposed within the actuator, wherein the sleeve includes slanted surface configured to engage with a corresponding angled surface of the actuator, wherein axial movement of the actuator relative to the sleeve causes the corresponding angled surface of the actuator to move the compression elements radially inwardly.

12. The device of claim 10,
   wherein the actuator is configured to actuate the crimping tool to radially crimp at least a portion of the collapsible device when the actuator is moved from a first predetermined position relative to the loading tool to a second predetermined position relative to the loading tool, wherein the rod is prevented from moving relative to the base of the expander while the actuator moves from the first predetermined position to the second predetermined position,
   wherein the actuator is configured to actuate the loading tool to load at least a portion of the collapsible device into the delivery system when the actuator is moved from the second predetermined position relative to the loading tool to a third predetermined position relative to the loading tool, wherein the rod moves axially through the base of the expander and into the central cavity while the actuator moves from the second predetermined position to the third predetermined position.

13. The device of claim 1, wherein the actuator includes a slanted surface configured to engage a corresponding slanted surface of the compression elements such that axial movement of the actuator relative to the loading tool causes the slanted surface to engage the corresponding slanted surface to push the compression elements radially inwardly.

14. The device of claim 13, further comprising a plate including a central opening therethrough, wherein the central opening is configured to slidingly receive the post of the loading tool.

15. The device of claim 14,
wherein the actuator is configured to actuate the crimping tool to radially crimp at least a portion of the collapsible device when the actuator is moved from a first predetermined position relative to the loading tool to a second predetermined position relative to the loading tool, wherein the rod is prevented from moving relative to the plate while the actuator moves from the first predetermined position to the second predetermined position, wherein the actuator is configured to actuate the loading tool to load at least a portion of the collapsible device into the delivery system when the actuator is moved from the second predetermined position relative to the loading tool to a third predetermined position relative to the loading tool, wherein the rod moves axially through the central opening of the plate and into the central cavity while the actuator moves from the second predetermined position to the third predetermined position.

16. The device of claim 14, wherein the loading tool further includes a plurality of fins configured to extend through corresponding openings through the plate.

17. The device of claim 16, wherein the fins are configured to engage the compression elements to maintain the compression elements in radially compressed when the loading tool moves axially relative to the actuator to move push the collapsible device out of the central cavity and into the delivery system.

* * * * *